United States Patent
Patel et al.

(10) Patent No.: US 12,016,666 B2
(45) Date of Patent: Jun. 25, 2024

(54) CARDIOVASCULAR MONITORING USING MULTIPLE SENSORS

(71) Applicant: Google LLC, Mountain View, CA (US)

(72) Inventors: Yojan Patel, London (GB); SeongHwan Cho, Mountain View, CA (US); Justin Phillips, London (GB)

(73) Assignee: Google LLC, Mountain View, CA (US)

( * ) Notice: Subject to any disclaimer, the term of this patent is extended or adjusted under 35 U.S.C. 154(b) by 1548 days.

(21) Appl. No.: 15/825,234

(22) Filed: Nov. 29, 2017

(65) Prior Publication Data
US 2019/0159690 A1 May 30, 2019

(51) Int. Cl.
*A61B 5/024* (2006.01)
*A61B 5/00* (2006.01)
(Continued)

(52) U.S. Cl.
CPC ...... *A61B 5/02416* (2013.01); *A61B 5/02438* (2013.01); *A61B 5/721* (2013.01);
(Continued)

(58) Field of Classification Search
CPC . A61B 5/02416; A61B 5/02438; A61B 5/721; A61B 5/0059; A61B 5/02108; A61B 5/02405; A61B 5/0295; A61B 5/681
See application file for complete search history.

(56) References Cited

U.S. PATENT DOCUMENTS 6,616,613 B1 * 9/2003 Goodman ............ A61B 5/0002
600/504
9,629,574 B2 4/2017 Lee
(Continued)

FOREIGN PATENT DOCUMENTS

CN 1646055 A 7/2005
CN 103052353 A 4/2013
(Continued)

OTHER PUBLICATIONS

Canino, N. K., Wang, R. R., & Robinson, C. J. (2016). Using multiple placements of accelerometers to measure cardiovascular pulse transit times. 2016 38th Annual International Conference of the IEEE Engineering in Medicine and Biology Society (EMBC). doi: 10.1109/embc.2016.7591665 (Year: 2016).*
(Continued)

*Primary Examiner* — Andrey Shostak
(74) *Attorney, Agent, or Firm* — Lerner David LLP

(57) ABSTRACT

A cardiovascular monitoring system includes a first monitoring device configured to couple to a first body part of a subject and a second monitoring device configured to couple to a second body part of the subject. The first monitoring device is configured to measure a first cardiovascular signal and a first motion signal at the first body part, and the second monitoring device is configured to measure a second cardiovascular signal and a second motion signal at the second body part. A controller of the system receives the first and second cardiovascular signals and the first and second motion signals and filters the first and second cardiovascular signals by removing spectral components that correspond to spectral components of the first and second motion signals. Based on a correlated spectral component that is present in both the filtered first and second cardiovascular signals, the system determines cardiovascular information of the subject.

12 Claims, 11 Drawing Sheets

(51) Int. Cl.
  *A61B 5/021* (2006.01)
  *A61B 5/0295* (2006.01)
(52) U.S. Cl.
  CPC ......... *A61B 5/0059* (2013.01); *A61B 5/02108* (2013.01); *A61B 5/02405* (2013.01); *A61B 5/0295* (2013.01); *A61B 5/681* (2013.01)

(56) References Cited

U.S. PATENT DOCUMENTS

| | | | |
|---|---|---|---|
| 9,814,400 B1 | 11/2017 | Cendrillon et al. | |
| 2006/0258927 A1 | 11/2006 | Edgar et al. | |
| 2009/0054752 A1* | 2/2009 | Jonnalagadda | A61B 5/721 600/324 |
| 2009/0105556 A1* | 4/2009 | Fricke | A61B 5/0205 600/301 |
| 2010/0160794 A1* | 6/2010 | Banet | A61B 5/02125 600/485 |
| 2012/0203077 A1* | 8/2012 | He | A61B 5/02125 600/301 |
| 2013/0184595 A1 | 7/2013 | Mukkamala et al. | |
| 2014/0275852 A1* | 9/2014 | Hong | A61B 5/02427 600/301 |
| 2015/0080746 A1* | 3/2015 | Bleich | G16H 20/30 600/479 |
| 2015/0100141 A1* | 4/2015 | Hughes | A61B 5/1118 700/92 |
| 2015/0313484 A1* | 11/2015 | Burg | A61B 5/021 600/301 |
| 2016/0051157 A1 | 2/2016 | Waydo | |
| 2016/0051158 A1* | 2/2016 | Silva | A61B 5/721 600/479 |
| 2016/0094899 A1 | 3/2016 | Aumer et al. | |
| 2017/0172510 A1 | 6/2017 | Homyk et al. | |
| 2017/0311825 A1 | 11/2017 | Weekly et al. | |
| 2018/0000363 A1* | 1/2018 | Pekonen | A61B 5/7475 |
| 2019/0254524 A1* | 8/2019 | Granqvist | A61B 5/0024 |

FOREIGN PATENT DOCUMENTS

| | | |
|---|---|---|
| CN | 106413530 A | 2/2017 |
| CN | 106560156 A | 4/2017 |
| CN | 107205667 A | 9/2017 |
| GB | 2547736 A | 8/2017 |
| GB | 2551201 A | 12/2017 |
| WO | 2017140663 A1 | 8/2017 |

OTHER PUBLICATIONS

PCT International Search Report and Written Opinion, PCT International Application No. PCT/US2018/061760, dated Feb. 22, 2019, 9 pages.
Warren, Kristen et al., "Improving Pulse Rate Measurements During Random Motion Using a Wearable Multichanne Reflectance Photoplethysmograph", Sensors, vol. 16, No. 3, Mar. 7, 2016, 18 pages.
Office Action for Chinese Patent Application No. 201880077465.3 dated Sep. 5, 2022. 8 pages.
Office Action for Chinese Patent Application No. 201880077465.3 dated Jun. 20, 2023. 9 pages.
Office Action for Chinese Patent Application No. 201880077465.3 dated Mar. 17, 2023. 9 pages.
Notice of Allowance for Chinese Patent Application No. 201880077465.3 dated Oct. 7, 2023. 5 pages.

* cited by examiner

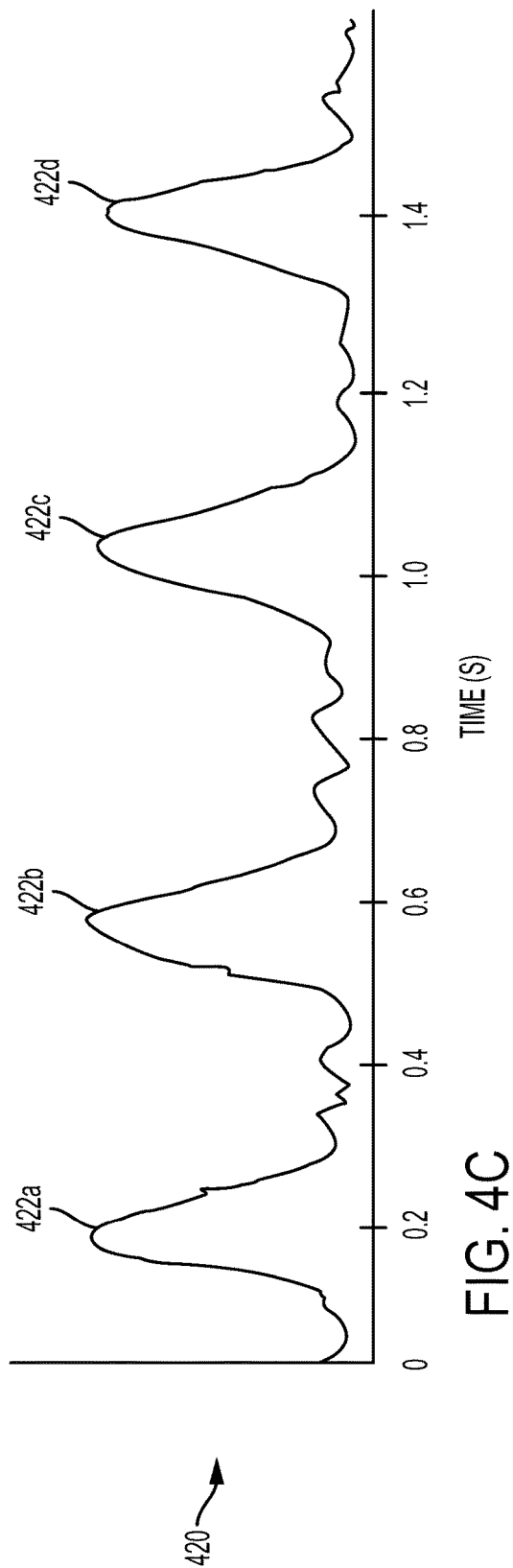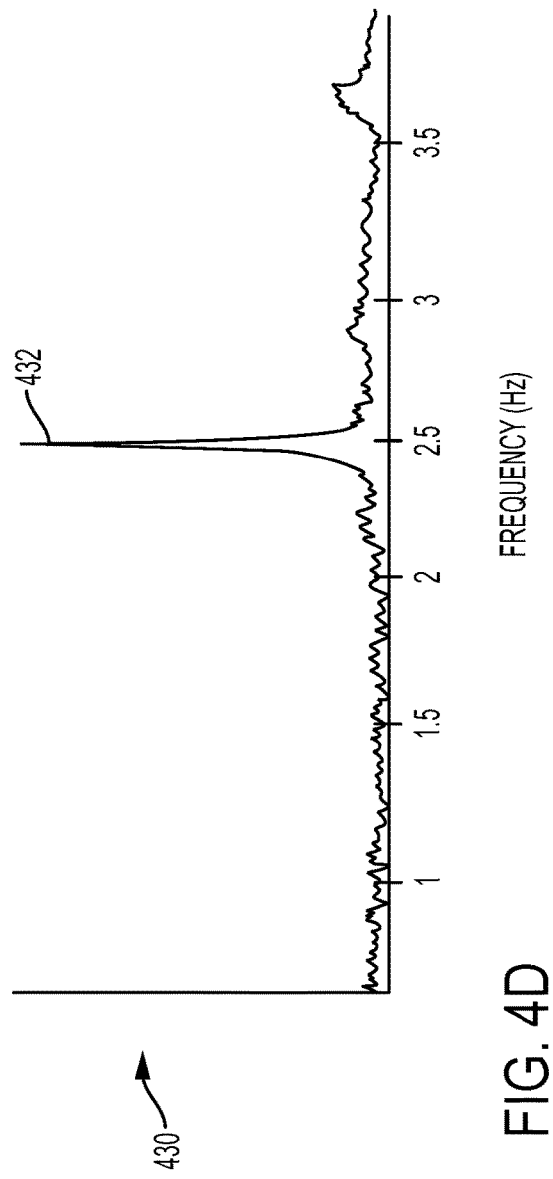
FIG. 4C
FIG. 4D

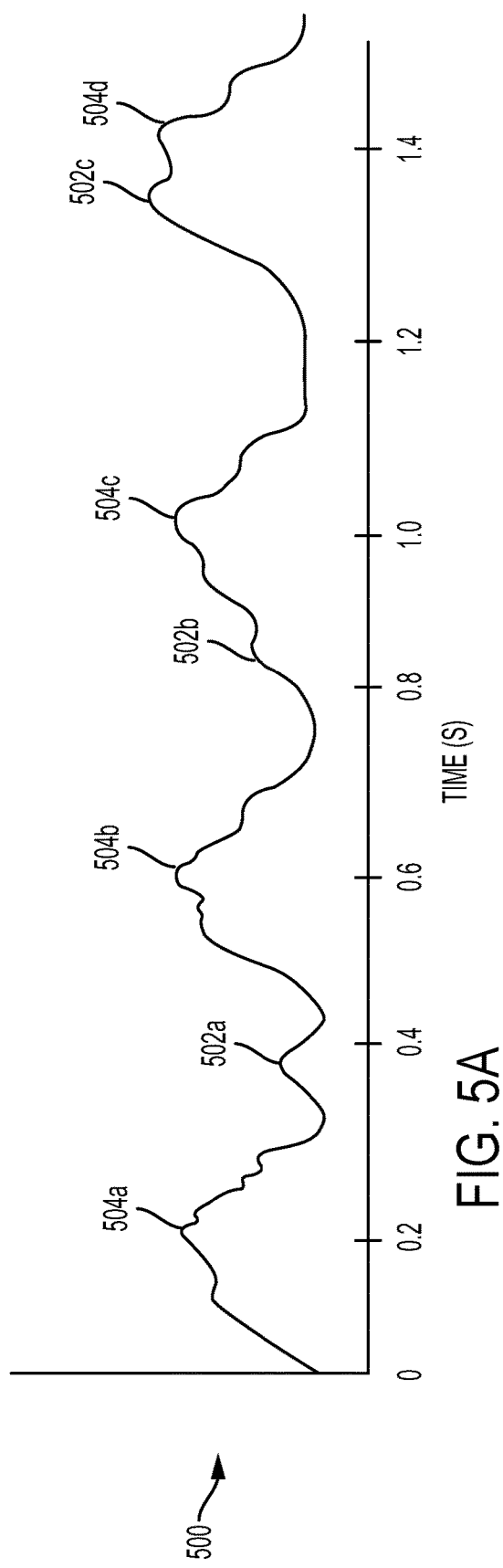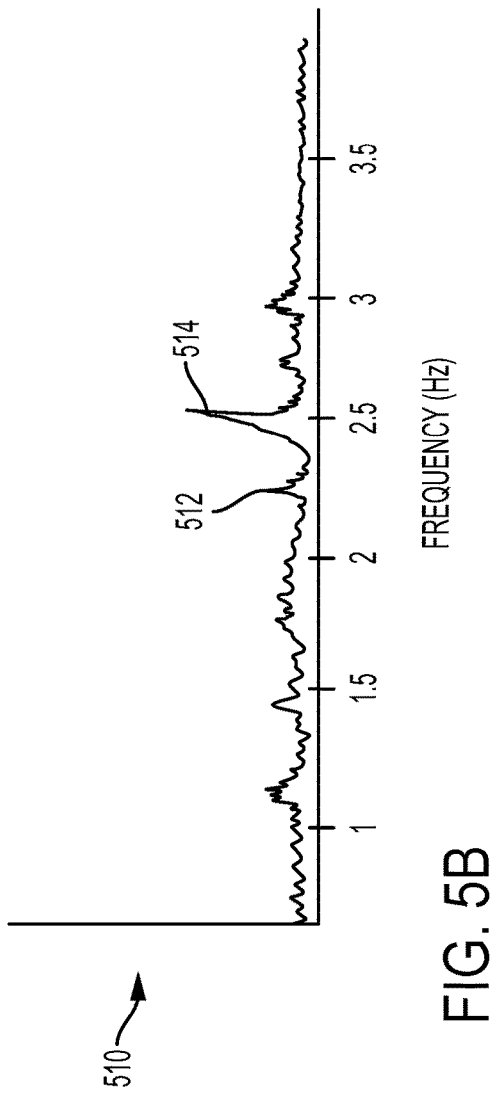
FIG. 5A
FIG. 5B

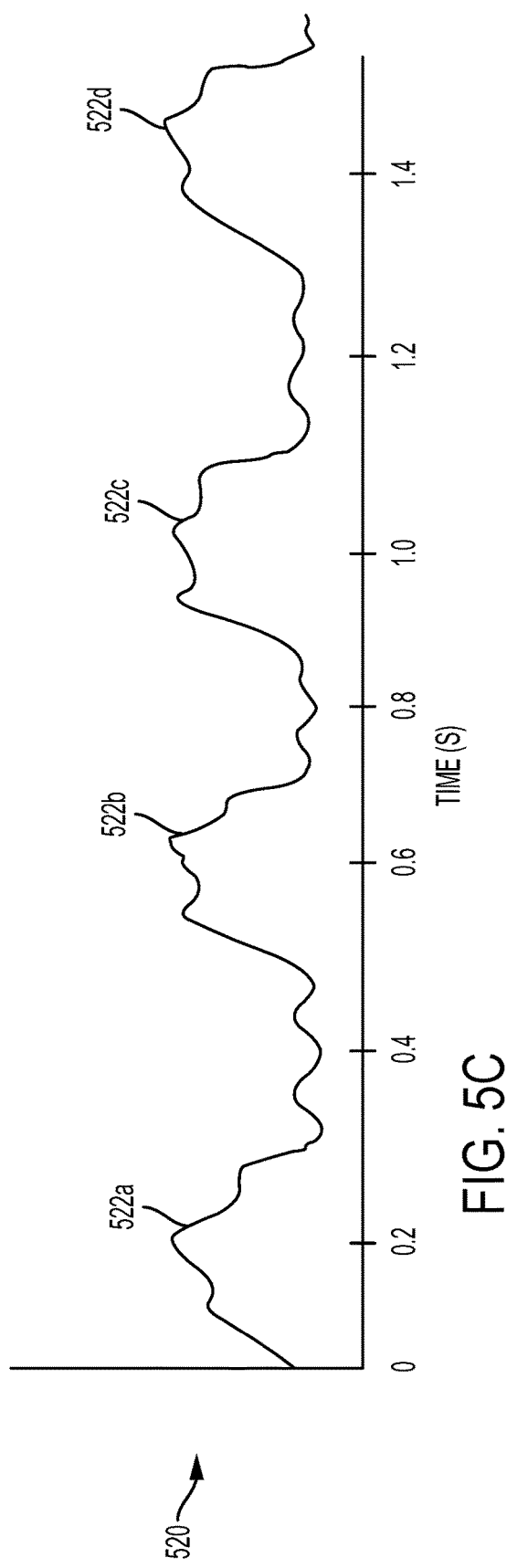
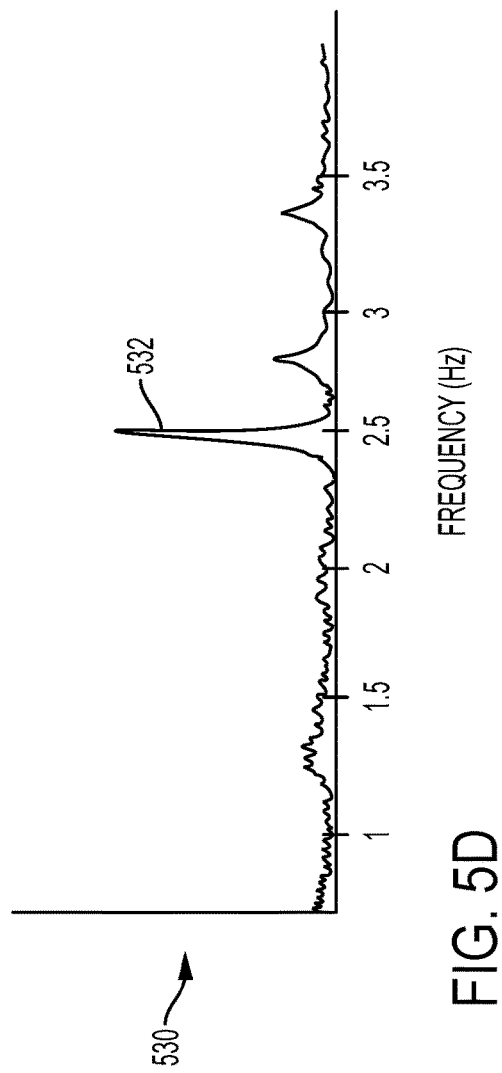
FIG. 5C
FIG. 5D

CARDIOVASCULAR MONITORING USING MULTIPLE SENSORS

BACKGROUND

Unless otherwise indicated herein, the materials described in this section are not prior art to the claims in this application and are not admitted to be prior art by inclusion in this section.

A heart rate of a person may be determined using a photoplethysmographic (PPG) sensor. Such a sensor typically includes one or more light sources and one or more detectors. During use, the one or more light sources may illuminate a portion of a person's skin. Blood flowing through vessels within the illuminated portion of the skin reflects a portion of the emitted light, which the one or more detectors may detect over a non-zero time period, thereby providing a PPG signal. A pulse or heart rate can thus be determined from the PPG signal, as changes in the intensity of the detected light correlate to changes in blood volume through the illuminated area resulting from the person's heart pumping blood.

SUMMARY

The present invention is directed to cardiovascular monitoring systems and related methods, in particular, cardiovascular monitoring systems that use multiple sensors to filter out unwanted signals.

In one aspect, a system is provided, comprising a first monitoring device configured to couple to a first body part of a subject, wherein the first monitoring device is configured to measure a first cardiovascular signal and a first motion signal at the first body part, and a second monitoring device configured to couple to a second body part of the subject, wherein the second monitoring device is configured to measure a second cardiovascular signal and a second motion signal at the second body part. The system further includes a controller configured to (i) receive the first and second cardiovascular signals and the first and second motion signals from the first and second monitoring devices, (ii) filter the first cardiovascular signal by removing one or more spectral components of the first cardiovascular signal that correspond to one or more spectral components of the first motion signal, (iii) filter the second cardiovascular signal by removing one or more spectral components of the second cardiovascular signal that correspond to one or more spectral components of the second motion signal, (iv) identify a correlated spectral component that is present in both the filtered first cardiovascular signal and the filtered second cardiovascular signal, and (v) determine, based on the correlated spectral component, cardiovascular information of the subject.

In another aspect a method is provided, comprising the steps of (i) receiving, from a first monitoring device coupled to a first body part of a subject, a first cardiovascular signal and a first motion signal indicative of one or more measurements obtained at the first body part, (ii) receiving, from a second monitoring device coupled to a second body part of the subject, a second cardiovascular signal and a second motion signal indicative of one or more measurements obtained at the second body part, (iii) filtering the first cardiovascular signal by removing one or more spectral components of the first cardiovascular signal that correspond to one or more spectral components of the first motion signal, (iv) filtering the second cardiovascular signal by removing one or more spectral components of the second cardiovascular signal that correspond to one or more spectral components of the second motion signal, (v) identifying a correlated spectral component that is present in both the filtered first cardiovascular signal and the filtered second cardiovascular signal, and (vi) determining, based on the correlated spectral component, cardiovascular information of the subject.

In yet another aspect a system is provided, comprising a first monitoring device configured to couple to a first body part of a subject, wherein the first monitoring device is configured to measure a first cardiovascular signal and a first motion signal at the first body part, and a second monitoring device configured to couple to a second body part of the subject, wherein the second monitoring device is configured to measure a second cardiovascular signal and a second motion signal at the second body part. The system further includes a controller configured to (i) receive the first and second cardiovascular signals and the first and second motion signals from the first and second monitoring devices, (ii) combine the received first and second cardiovascular signals, (iii) filter the combined cardiovascular signals by removing one or more spectral components of the combined cardiovascular signals that correspond to one or more spectral components of the first and second motion signals, and (iv) determine, based on a remaining spectral component of the filtered combined cardiovascular signals, cardiovascular information of the subject.

In yet another aspect a system is provided, comprising a first monitoring device configured to couple to a first body part of a subject, wherein the first monitoring device includes means for measuring a first cardiovascular signal and a first motion signal at the first body part, and a second monitoring device configured to couple to a second body part of the subject, wherein the second monitoring device includes means for measuring a second cardiovascular signal and a second motion signal at the second body part. The system further includes means for (i) receiving the first and second cardiovascular signals and the first and second motion signals from the first and second monitoring devices, (ii) filtering the first cardiovascular signal by removing one or more spectral components of the first cardiovascular signal that correspond to one or more spectral components of the first motion signal, (iii) filtering the second cardiovascular signal by removing one or more spectral components of the second cardiovascular signal that correspond to one or more spectral components of the second motion signal, (iv) identifying a correlated spectral component that is present in both the filtered first cardiovascular signal and the filtered second cardiovascular signal, and (v) determining, based on the correlated spectral component, cardiovascular information of the subject.

In yet another aspect a system is provided, comprising a first monitoring device configured to couple to a first body part of a subject, wherein the first monitoring device includes means for measuring a first cardiovascular signal and a first motion signal at the first body part, and a second monitoring device configured to couple to a second body part of the subject, wherein the second monitoring device includes means for measuring a second cardiovascular signal and a second motion signal at the second body part. The system further includes means for (i) receiving the first and second cardiovascular signals and the first and second motion signals from the first and second monitoring devices, (ii) combining the received first and second cardiovascular signals, (iii) filtering the combined cardiovascular signals by removing one or more spectral components of the combined cardiovascular signals that correspond to one or more spectral components of the first and second motion signals, and (iv) determining, based on a remaining spectral component of the filtered combined cardiovascular signals, cardiovascular information of the subject.

These as well as other aspects, advantages, and alternatives, will become apparent to those of ordinary skill in the art by reading the following detailed description, with reference where appropriate to the accompanying drawings.

BRIEF DESCRIPTION OF THE DRAWINGS

FIG. 4C is a plot of a first motion signal, according to an example embodiment.

FIG. 4D is a frequency spectra plot of the first motion signal, according to an example embodiment.

FIG. 5A is a plot of a second photoplethysmography signal, according to an example embodiment.

FIG. 5B is a frequency spectra plot of the second photoplethysmography signal, according to an example embodiment.

FIG. 5C is a plot of a second motion signal, according to an example embodiment.

FIG. 5D is a frequency spectra plot of the second motion signal, according to an example embodiment.

DETAILED DESCRIPTION

The following detailed description describes various features and functions of the disclosed systems and methods with reference to the accompanying figures. In the figures, similar symbols typically identify similar components unless context dictates otherwise. The illustrative system and method embodiments described herein are not meant to be limiting. It will be readily understood that certain aspects of the disclosed systems and methods can be arranged and combined in a wide variety of different configurations, all of which are contemplated herein.

I. Overview

Cardiovascular monitoring devices may collect data relating to a subject's cardiovascular function. Such data may include data relating to pulse, blood flow, blood pressure, and/or other indicators of cardiovascular function. For instance, the cardiovascular monitoring devices may include one or more photoplethysmography (PPG) sensors that collect data relating to changes in blood volume in a body part as the subject's heart pumps blood.

The cardiovascular monitoring devices may be coupled to different parts of the subject's body in order to collect this data. Motion of the body parts during data collection can introduce motion-related artifacts into the collected data. In other words, in addition to collecting data relating to the subject's cardiovascular function, the cardiovascular monitoring devices may detect signals that result from motion of the body parts to which the devices are coupled to. Motion-related artifacts may obscure, distort, or misrepresent the actual cardiovascular data.

Advantageously, the example systems can process the collected data to remove or minimize the motion-related artifacts, allowing cardiovascular functions to be more accurately evaluated based on the collected data. In particular, the example systems may collect data simultaneously from multiple monitoring devices. For example, the monitoring devices may be coupled to different body parts, and each monitoring device may measure cardiovascular signals and motion signals at their respective body parts. Each monitoring device can filter its measured cardiovascular signals to remove one or more spectral components of its measured motion signals. This may remove some or all of the motion-related artifacts in each respective cardiovascular signal while leaving spectral components associated with the subject's heart rate unaltered. Accordingly, because each filtered cardiovascular signal includes a spectral component corresponding to the subject's heart rate, the subject's heart rate may be determined by identifying a spectral component that is present in all of the filtered cardiovascular signals.

II. Example Cardiovascular Monitoring Systems and Devices

Figure 1:
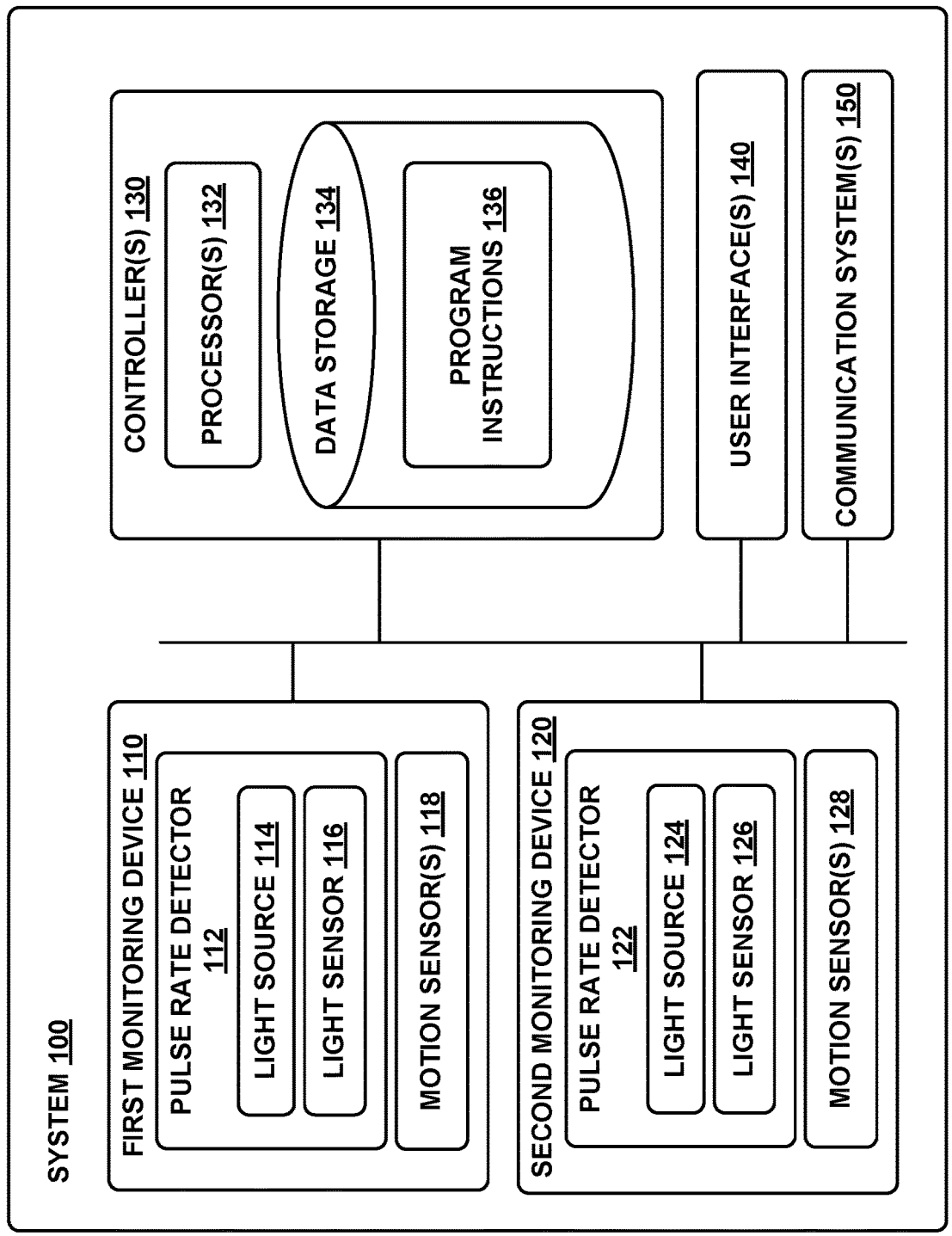
FIG. 1 is a simplified block diagram of a cardiovascular monitoring system, according to an example embodiment.

FIG. 1 is a simplified block diagram of a cardiovascular monitoring system 100. The system 100 may include a first monitoring device 110, a second monitoring device 120, one or more controllers 130, one or more user interfaces 140, and one or more communication systems 150 for transmitting data between components of the system 100 and/or to another system, such as a remote server, a cloud computing system, or some other computing device.

The first monitoring device 110 may be a wearable device configured to measure a cardiovascular pulse rate of blood in a portion of subsurface vasculature (or of some other tissue or cells) of a person wearing the device. The term "wearable device," as used in this disclosure, refers to any device that is capable of being worn at, on, or in proximity to a body surface, such as a wrist, ankle, waist, chest, or other body part. In order to take in vivo measurements in a non-invasive manner from outside of the body, the wearable device may be positioned on a portion of the body where subsurface vasculature or some other tissue containing pulsatile blood flow is observable. The device may be placed in close proximity to the skin or tissue, but need not be touching or in intimate contact therewith.

The first monitoring device 110 includes a pulse rate detector 112. The pulse rate detector 112 may take the form of a PPG system and may include a light source 114 and a light sensor 116. The light source 114 may emit illumination into a portion of the subject's subsurface vasculature, and the light sensor 116 may detect one or more properties of light emitted from the portion of subsurface vasculature in response to illumination emitted from the light source 114. In a non-exhaustive list, the light sensor 116 may include one or more of a photodiode, a phototransistor, a photoresistor, an active pixel sensor, a CCD, a camera, a spectrometer, an interferometer, or some other light sensitive element configured to detect one or more properties of the emitted light, and could potentially include one or more light sources as well.

The first monitoring device 110 also includes one or more motion sensors 118 for measuring movement of the first monitoring device 110. The motion sensor(s) 118 may be configured to output one or more signals based on a motion of the first monitoring device 110. For instance, the motion sensor(s) 118 may include one or more accelerometers, inertial measurement units (IMUs), or the like.

The second monitoring device 120 may also be a wearable device configured to measure a cardiovascular pulse rate of a person wearing the device, and the second monitoring device 120 may be worn concurrently with the first monitoring device 110 by the same person. For example, the second monitoring device 120 may be worn by the person at or on a different body part than the first monitoring device 110.

Similar to the first monitoring device 110, the second monitoring device 120 also includes a pulse rate detector 122 and one or more motion sensors 128. The pulse rate detector 122 and the motion sensor(s) 128 of the second monitoring device 120 may operate in the same or in a similar manner as the pulse rate detector 112 and the motion sensor(s) 118 of the first monitoring device 110. As such, the pulse rate detector 122 of the second monitoring device 120 may take the form of a PPG system and may include a light source 124 configured to emit illumination into a portion of the subject's subsurface vasculature, and a light sensor 126 configured to detect one or more properties of the light emitted from the light source 124. And the motion sensor(s) 128 may include one or more accelerometers or IMUs configured to output one or more signals based on a motion of the second monitoring device 120.

As noted above, the system 100 includes one or more controllers 130. The controller(s) 130 include one or more processors 132, which may include or take the form of a central processing unit (CPU), such as one or more general purpose processors and/or one or more dedicated processors (e.g., application specific integrated circuits (ASICs) or digital signal processors (DSPs), etc.). The controller(s) 130 further include data storage 134, which may include or take the form of one or more non-transitory computer-readable storage media that can be read or accessed by the processor(s) 132. The one or more computer-readable storage media can include volatile and/or non-volatile storage components, such as optical, magnetic, organic, or other memory or disc storage. In some embodiments, the data storage 134 can be implemented using a single physical device (e.g., one optical, magnetic, organic, or other memory or disc storage unit), while in other embodiments, the data storage 134 can be implemented using two or more physical devices.

The processor(s) 132 can be configured to execute computer-readable program instructions 136 that are stored in the data storage 134 and are executable to provide some or all of the functionality described herein. For instance, the processor(s) 132 can execute the computer-readable program instructions 136 to operate the pulse rate detectors 112, 122 and the motion sensor(s) 118, 128 of the first and second monitoring devices 110, 120, as described in further detail below.

The user interface(s) 140 of the system 100 may include indicators, displays, buttons, touchscreens, head-mounted displays, and/or other elements configured to present information about the system 100 to a user and/or to allow the user to operate the system 100. Additionally or alternatively, the system 100 could be configured to communicate with another system (e.g., a cellphone, a tablet, a computer, a remote server) and to present elements of a user interface using the remote system. The user interface(s) 140 could be configured to allow a user to specify some operation, function, or property of operation of the system 100. The user interface(s) 140 could be configured to present a determined pulse rate of blood in a portion of subsurface vasculature or some other health state of a wearer of the first and second monitoring devices 110, 120, or to present some other information to a user. Other examples are possible as well.

The communication system 150 may include one or more wired or wireless interfaces for communicating data between various components of the system 100 and/or for communicating with one or more other computing systems. For instance, the communication system 150 may include one or more antennas for transmitting and/or receiving an electromagnetic or other wireless signal according to one or more wireless communications standards (e.g., Bluetooth, WiFi, IRdA, ZigBee, WiMAX, or LTE). Additionally or alternatively, the communication system 150 may include one or more wired communications interfaces for sending and/or receiving signals according to one or more wired communications standards (e.g., USB, FireWire, Ethernet, or RS-232).

In practice, the controller(s) 130 could communicate via the communication system 150 with the first and second monitoring devices 110, 120 to receive signals generated by their pulse rate detectors 112, 122 and motion sensor(s) 118, 128. The controller(s) 130 could perform operations on the received signals to determine cardiovascular information, such as a heart pulse rate, of a subject as described in further detail below. Further, the controller(s) 130 could communicate via the communication system 150 to provide an output of the determined cardiovascular information. For instance, the controller(s) 130 could communicate with the user interface(s) 140 to cause the user interface(s) 140 to display a graphical or textual representation of the determined cardiovascular information. Additionally or alternatively, the controller(s) 130 could use the communication system 150 to send information related to the determined cardiovascular information over a communication network, such as the Internet, to an external computing system, such as a cloud computing system and/or a remote server. As such, the cardiovascular information could be stored on the external computing system for remote access and/or for further processing.

It should be understood that the system 100 depicted in FIG. 1 is simplified for illustration purposes and that implementation of the system 100 may be carried out in various ways. Accordingly, some or all of the components of the system 100 may be implemented as part of a single device or across multiple devices. For example, all or part of the controller(s) 130, user interface(s) 140, and/or communication system(s) 150 may be implemented as part of one or both of the first and second monitoring devices 110, 120. Other examples are possible as well.

Figure 2A:
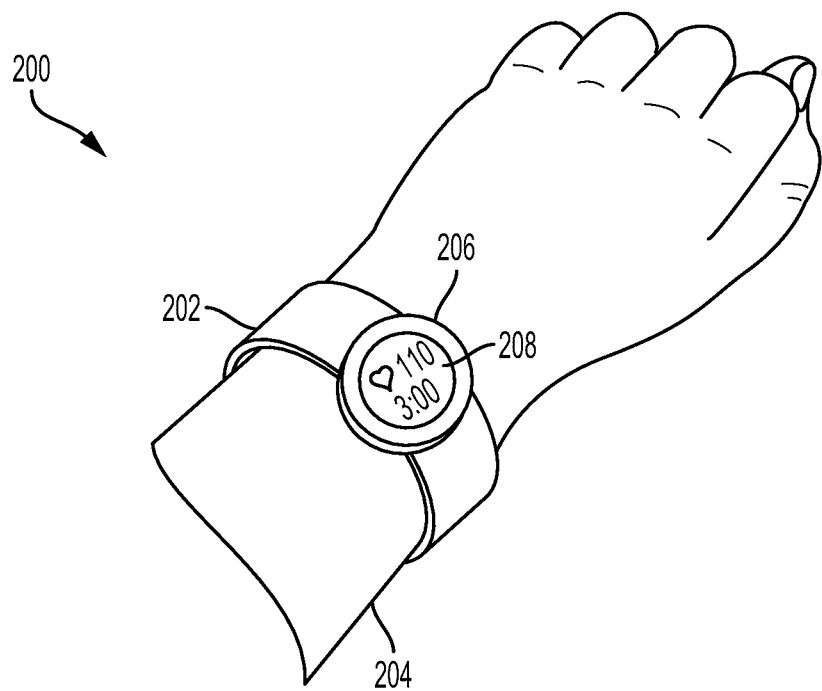
FIG. 2A illustrates a wrist-mountable device, according to an example embodiment.
Figure 2B:
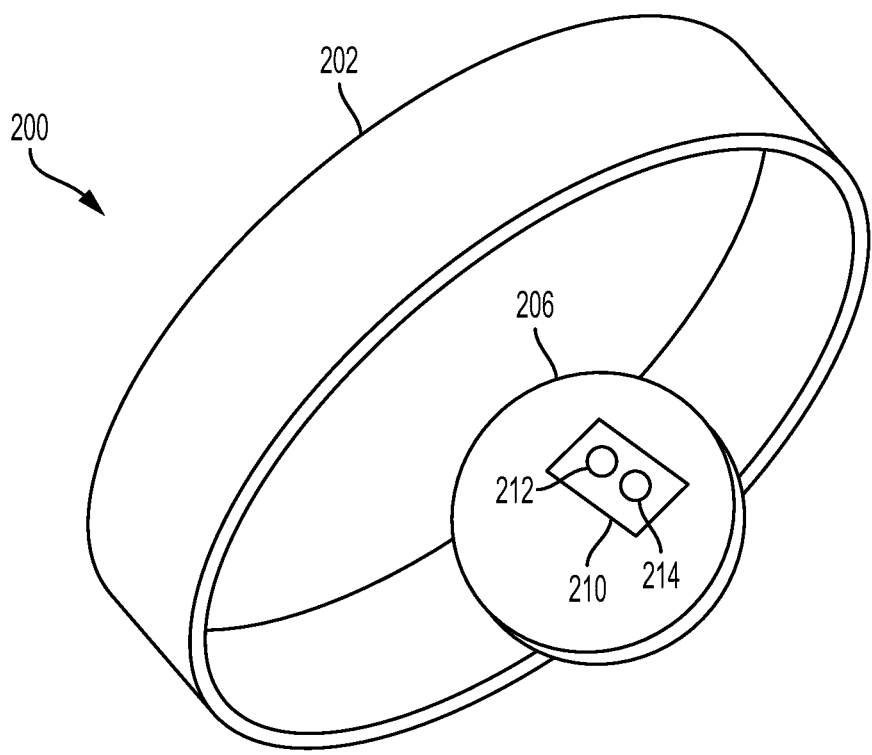
FIG. 2B illustrates the wrist-mountable device shown in FIG. 2A, according to an example embodiment.

FIGS. 2A and 2B illustrate an example wearable device 200 for monitoring cardiovascular activity of a subject wearing the device 200. The wearable device 200 may be used as the first or second monitoring device 110, 120 described above with respect to the system 100 depicted in FIG. 1. As shown, the wearable device 200 is a wrist-mountable device (e.g., a wristwatch) that includes a mount 202 for mounting the device 200 to a wrist 204 of the subject. The mount 202 may take the form of a strap or band that can be wrapped around the wrist 204, or the mount 202 may include an adhesive substrate for adhering the wearable device 100 to the wrist 204 of the subject.

The wearable device 200 may further include a housing 206 that includes a display 208 through which the subject may receive one or more indications or alerts. For example, the display 208 may include a liquid crystal display (LCD) screen or the like configured to indicate, through textual or graphical information, a heart rate of the subject and/or a time of day. The housing 206 may include various other components for facilitating operation of the wearable device 200, such as a controller, data storage, and/or a communication interface for communicating with various other computing devices.

As shown in FIG. 2B, a PPG sensor 210 may be disposed in an underside of the housing 206 so that the PPG sensor 210 faces the wrist 204 of the subject. The PPG sensor 210 includes a light source 212 and a light sensor 214. The light source 212 may be configured to emit illumination into a portion of subsurface vasculature of the subject, and the light sensor 214 may be configured to detect an intensity or other properties of light emitted from (e.g., reflected from, refracted by, scattered by) the portion of subsurface vasculature in response the illumination emitted from the light source 212. Based on the light detected by the light sensor 214, the device 200 may detect changes in blood volume in the subsurface vasculature as the subject's heart pumps blood. Because the detected changes in blood volume correspond to pulses of the subject's heart, the device 200 can use these detections to determine the subject's pulse rate.

To facilitate this, the light source 212 may include a light-emitting diode (LED), a laser, or some other light source configured to transmit illumination that can penetrate the wearer's skin into the portion of subsurface vasculature, for example, into a lumen of the subsurface vasculature. In some examples, the light source 212 may include multiple light sources, and each respective light source could be configured to emit a respective frequency of light that is the same as or different from the frequencies of the other respective light sources. In any case, the transmitted illumination can be any kind of illumination that is benign to the wearer and that results at least in an amount of absorption by blood in the subsurface vasculature that is related to the volume of the blood in the subsurface vasculature, e.g., such that light responsively emitted from the body has one or more detectable properties related to the volume of flow and/or the pulse rate of blood in the portion of subsurface vasculature (e.g., an intensity related to the amount of blood in the portion of subsurface vasculature). The wavelength of the transmitted illumination could be specified to penetrate biological tissues of a wearer and could also be specified to be a wavelength that is absorbed and/or scattered by blood cells. For example, the wavelength of the transmitted illumination could be a wavelength in the visible or near-infrared spectrum (e.g., between 400 nanometers and 1000 nanometers).

The light sensor 214 may include one or more of a photodiode, a phototransistor, a photoresistor, an active pixel sensor, a CCD, a camera, a spectrometer, an interferometer, or some other light sensitive element configured to detect one or more properties of the emitted light. The components of the PPG sensor 210 may be miniaturized so that the wearable device 200 may be worn by the subject without significantly interfering with the subject's usual activities.

In line with the discussion above, the wearable device 200 may further include one or more motion sensors (not shown). For instance, the housing 206 may include one or more IMUs or accelerometers configured to adjust an output signal, such as a voltage or current, based on motion of the device 200. As such, the motion sensors of the wearable device 200 may output a time-varying signal when undergoing movement, such as when the subject is swinging his or her arms while running. Other examples are possible as well.

Figure 3:
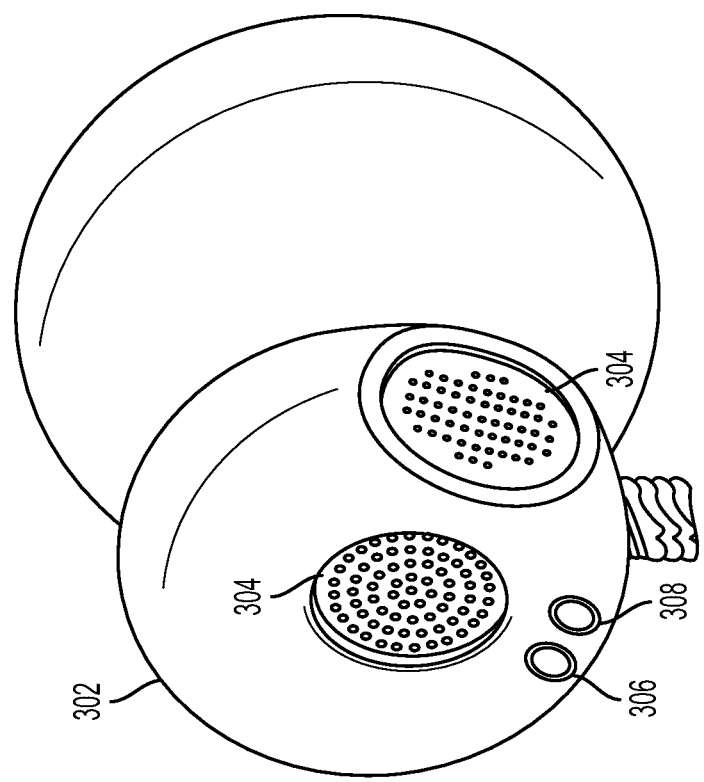
FIG. 3 illustrates an ear-mountable device, according to an example embodiment.
Figure 3:
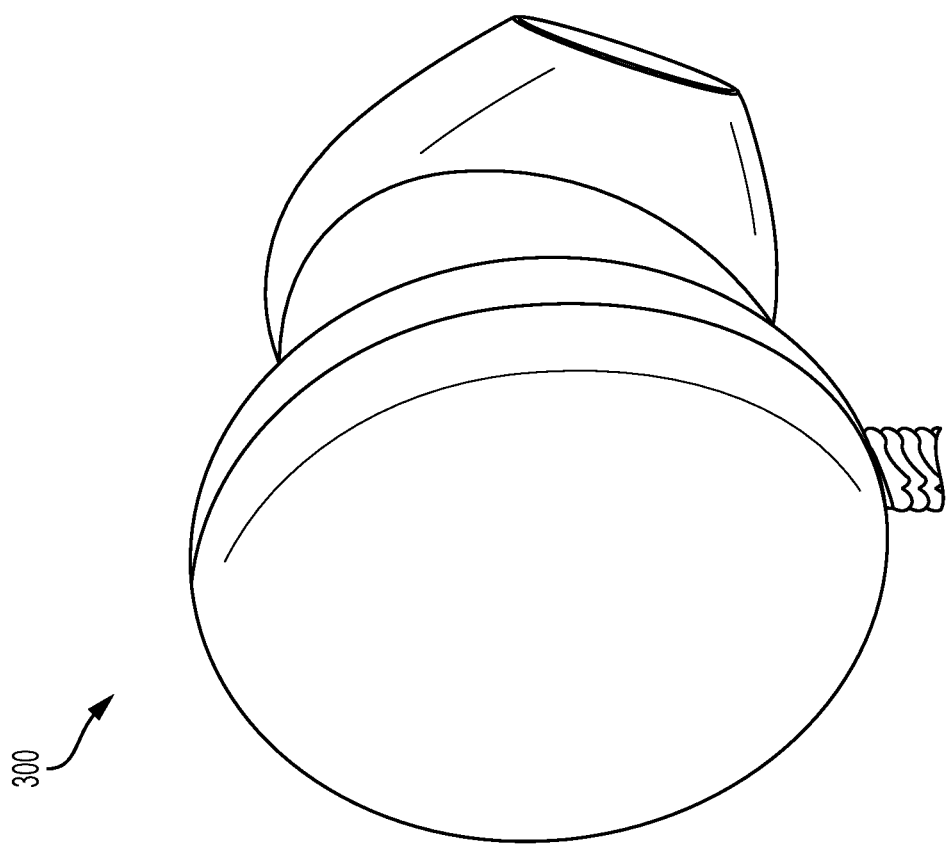

FIG. 3 illustrates another example wearable device 300 for monitoring cardiovascular activity of a subject wearing the device 300. Like the wearable device 200 depicted in FIGS. 2A and 2B, the wearable device 300 may be used as the first or second monitoring device 110, 120 described above with respect to the system 100 depicted in FIG. 1. As shown, the wearable device 300 is an ear-mountable device (e.g., earbuds) that includes a housing 302 shaped so as to be insertable into a portion of the subject's ear. The housing 302 may include various components, such as a controller and data storage, for facilitating operation of the device 300.

In some examples, the wearable device 300 includes one or more speakers 304 disposed in the housing 302. The speakers 304 may be configured to output an audio signal, such as a music signal, that is provided to the wearable device 300 via a wired or wireless communication interface. The speakers 304 may be arranged in the housing 302 so that when the housing 302 is mounted to the subject's ear, the speakers 304 can output an audio signal that is directed into the subject's ear canal.

As further shown, the wearable device 300 may include a pulse detection system. For instance, the device 300 may include a light source 306 and a light sensor 308 arranged in the housing 302 of the device 300. The light source 306 and the light sensor 308 may be similar to those described above, and the wearable device 300 may similarly use the light source 306 and 308 to detect a pulse rate of the subject. In such a scenario, the light source 306 would emit light toward a subsurface vasculature in the subject's ear, and the light sensor 308 would detect light reflected from and/or scattered by the subsurface vasculature.

Additionally, the wearable device 300 may further include one or more motion sensors, such as one or more IMUs or accelerometers arranged within the housing 302 of the device 300. As described above, the motion sensors may be configured to adjust an output signal, such as a voltage or current, based on motion of the device 300. As such, the motion sensors of the wearable device 300 may output a time-varying signal when undergoing movement, such as when the subject's head is bouncing up and down while running. Other examples are possible as well.

III. Example Embodiments for Processing Collected Data

Figure 4A:
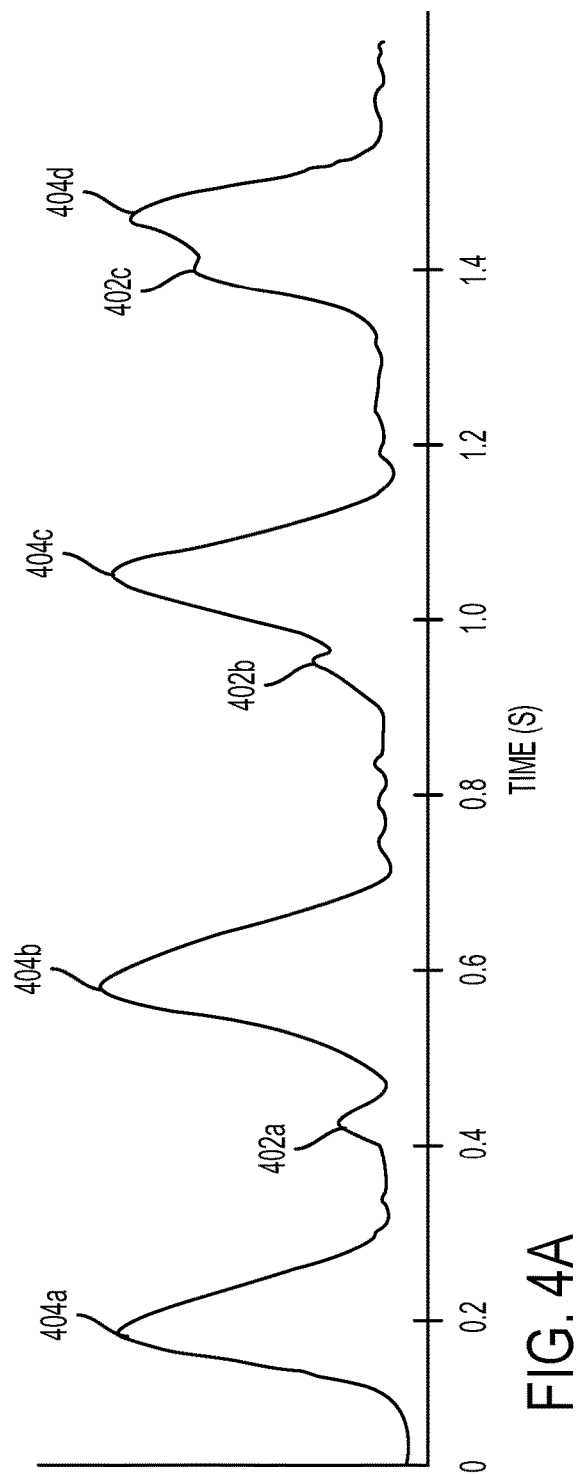
FIG. 4A is a plot of a first photoplethysmography signal, according to an example embodiment.

FIG. 4A illustrates an example signal 400 output by a light sensor of a wrist-mountable device, such as the wearable device 200 depicted in FIG. 2. As noted above, the light sensor may output a signal based on an intensity of light reflected from a subsurface vasculature of the subject. As the blood volume of the subsurface vasculature changes due to the subject's heart pumping, so does the amount of light that is reflected therefrom and detected by the light sensor. Accordingly, the signal 400 includes a number of peaks 402a-c that correspond with changes in reflected light caused by changes in blood volume in the subsurface vasculature and, thus, correspond with a heart rate of the subject.

However, as further shown, the signal 400 includes a number of other peaks 404a-d that do not correspond with the subject's heart rate, but are instead artifacts caused by motion. These artifacts may arise when the light sensor and/or the light source move relative to the subject. For instance, when the light sensor is moved farther away and/or angled away from the subject's subsurface vasculature, the light sensor may detect less light reflected from the vasculature, and/or the light sensor may detect light that is incident on the light sensor from alternative sources, such as ambient light. Similarly, when the light source is moved farther away and/or angled away from the subject's subsurface vasculature, the amount of light incident on the subject's subsurface vasculature may be reduced, thereby reducing the amount of light detected by the light sensor.

In a wrist-mountable device, these motion artifacts 404a-d could arise, for example, when the subject is swinging his or her arms while running. Other examples are possible as well. If the wrist-mountable device is not secured tightly around the subject's wrist, then the device may be jostled, and the motion artifacts 404a-d may be seen on the output signal 400 of the light sensor.

As shown in FIG. 4A, when the motion of the device is substantial, the motion artifacts 404a-d of the light sensor output may be larger in magnitude than the heart rate peaks 402a-c. As a result, it may be difficult to determine the subject's pulse rate from the signal 400. For example, the wearable device may be configured to determine the subject's pulse rate based on a frequency of peaks in the light sensor output signal 400. In some examples, the heart rate may be measured by counting the number of signal peaks within a time window or by determining a fundamental frequency or second harmonic of the signal by using a spectral estimation algorithm, such as a fast Fourier transform (FFT) algorithm.

Figure 4B:
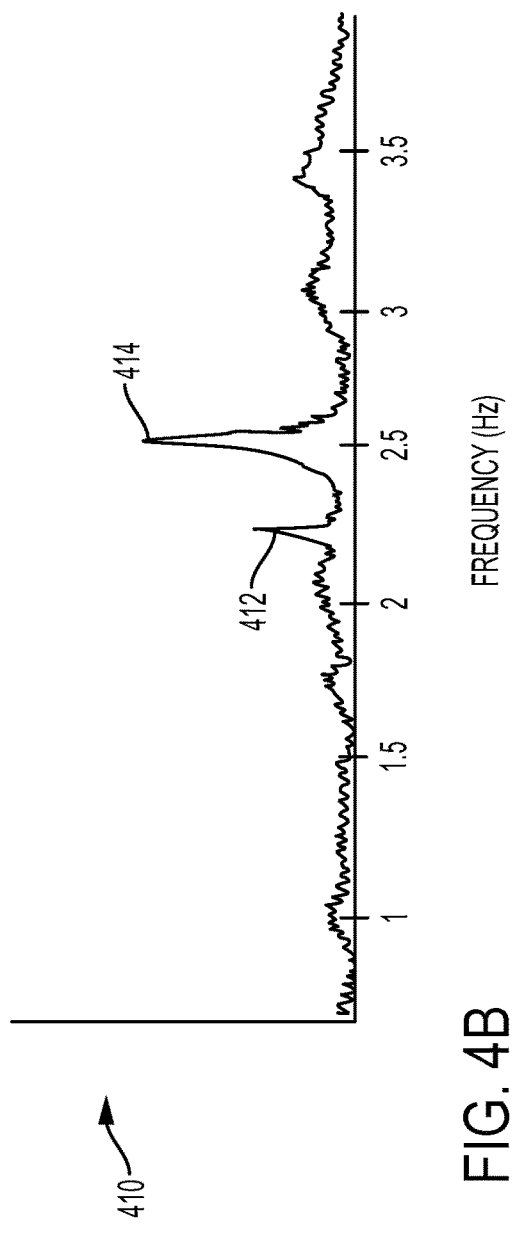
FIG. 4B is a frequency spectra plot of the first photoplethysmography signal, according to an example embodiment.

FIG. 4B illustrates an example frequency spectra plot 410 of the light sensor output 400, which may be obtained using an FFT algorithm. It should be understood that the frequency spectra plot 410 is for illustrative purposes only and may not be an exact representation of the spectral components of the light sensor output 400. The frequency spectra plot 410 includes a heart rate frequency peak 412 corresponding to a frequency of the heart rate peaks 402a-c, and the frequency spectra plot 410 includes a motion frequency peak 414 corresponding to a frequency of the motion artifacts 404a-d. Without the motion artifacts 404a-d or with substantially small motion artifacts, the heart rate frequency peak 412 would be the dominant frequency peak, and the wearable device could use the frequency spectra plot 410 to determine the heart rate of the subject by merely identifying the dominant frequency in the frequency spectra plot 410. However, when the motion artifacts 404a-d are similar in magnitude and/or larger in magnitude than the heart rate peaks 402a-c, it may be difficult for the wearable device to distinguish between the two. As shown, for instance, the heart rate frequency peak 412 occurs at approximately 2.25 Hz, and the motion frequency peak 414 occurs at approximately 2.5 Hz. Because the 2.5 Hz motion frequency peak 414 is the dominant peak, the wearable device could mistakenly determine that the subject's heart rate is 2.5 Hz (or 150 beats per minute (bpm)), but in reality the subjects heart rate is 2.25 Hz (or 135 bpm) as shown by the smaller heart rate frequency peak 412.

To compensate for such inaccuracies, the wearable device may be configured to take into consideration a motion of the device when determining the subject's heart rate. As noted above, the device may include one or more motion sensors, such as an IMU or an accelerometer, configured to adjust an output signal based on motion of the device.

FIG. 4C illustrates an example signal 420 output by a motion sensor of a wrist-mountable device, such as the wearable device 200 depicted in FIG. 2. As shown, the motion sensor output signal 420 may include a number of peaks 422a-d corresponding to motion of the wearable device. For instance, if the subject is wearing the device on his or her wrist while running, then the peaks 422a-d may correspond to each time the subject swings his or her arm. Other examples are possible as well. Because the motion artifacts 404a-d in the light sensor output signal 400 correspond to motion of the wearable device, the motion artifacts 404a-d should have a similar occurrence frequency as the peaks 422a-d in the output signal 420 of the motion sensor.

FIG. 4D illustrates an example frequency spectra plot 430 of the motion sensor output 420, which may be obtained using an FFT algorithm. Again, it should be understood that the frequency spectra plot 430 is for illustrative purposes only and may not be an exact representation of the spectral components of the motion sensor output 420. The frequency spectra plot 430 includes a peak 432 corresponding to a dominant frequency of the motion sensor output 420, which corresponds to the frequency of the peaks 422a-d of the motion sensor output 420. By comparing the frequency spectra plot 430 of the motion sensor output 420 with the frequency spectra plot 410 of the light sensor output 400, it can be seen that frequency peak 432 of the motion sensor frequency spectra plot 430 aligns with frequency peak 414 of the light sensor frequency spectra plot 410.

As such, the frequency spectra 430 of the motion sensor output 420 may be used to filter the light sensor output signal 400 and/or the frequency spectra 410 of the light sensor output signal 400 in order to remove some or all of the motion artifacts 404a-d. For instance, the wearable device may identify one or more spectral components of the motion sensor output 420 (e.g., by using an FFT algorithm to identify one or more dominant frequencies of the motion sensor output 420), and the wearable device may then filter the light sensor output signal 400 and/or the frequency spectra signal 410 to remove the identified spectral components. In the illustrated examples, the wearable device may identify 2.5 Hz as a dominant frequency of the motion sensor output signal 420 based on the frequency peak 432 occurring at 2.5 Hz. As such, the wearable device could filter the light sensor output signal 400 to remove frequencies at or near 2.5 Hz. For instance, the wearable device could pass the light sensor output signal 400 through a band-pass, low-pass, or high-pass filter, which could be implemented in hardware and/or software.

Figure 4E:
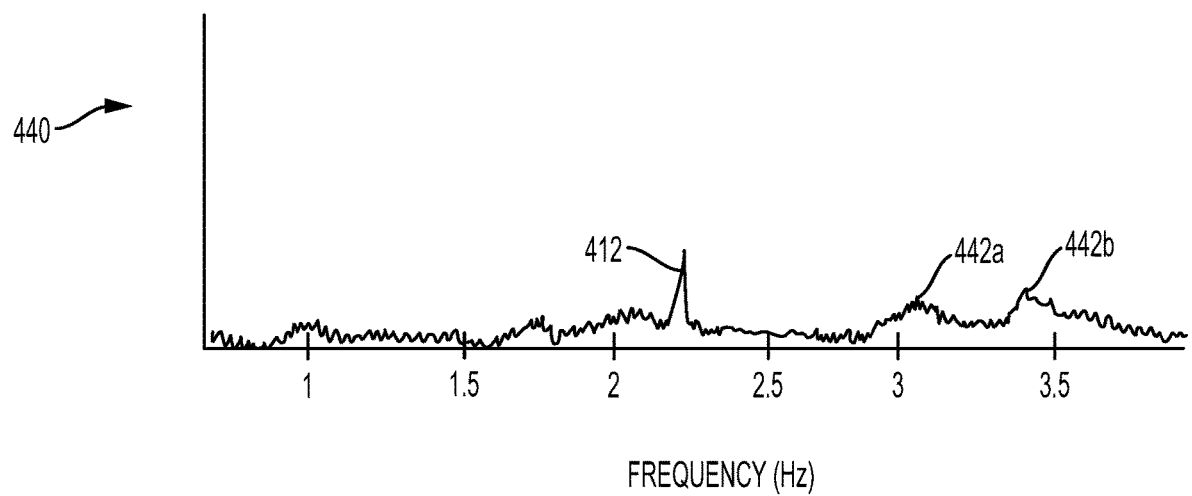
FIG. 4E is a frequency spectra plot of the first photoplethysmography signal after filtering, according to an example embodiment.

FIG. 4E illustrates an example frequency spectra plot 440 of the light sensor output 400 after filtering the light sensor output 400 to remove the spectral components identified from the motion sensor output 420. As shown, the filtered frequency spectra plot 440 includes the frequency peak 412 corresponding to the frequency of the heart rate peaks 402a-c. Noticeably, the frequency peak 414 corresponding to the frequency of the motion artifacts 404a-d is no longer present. Thus, performing this filtering process can improve the quality of the light sensor output signal 400 by removing some of the motion artifacts, such as those corresponding to peaks 404a-d. However, other artifacts may still remain, such as artifacts related to motion that is not detected by the motion sensor of the wearable device and/or motion artifacts that were detected but not entirely filtered out. For instance, as shown, the filtered frequency spectra plot 440 includes additional spectral components 442a-b that may be misinterpreted as a heart rate of the subject.

In order to further compensate for these additional artifacts, the subject may be outfitted with multiple cardiovascular monitoring devices, and the multiple devices may work in tandem to determine the subject's heart rate. For example, in addition to wearing a wrist-mountable device, such as the wrist-mountable device 200 depicted in FIG. 2, the subject could also wear an ear-mountable device, such as the ear-mountable device 300 depicted in FIG. 3.

In line with the discussion above, the ear-mountable device may include a light source and a light sensor for detecting changes in blood volume in subsurface vasculature in the subject's ear, and the device may further include one or more motion sensors for detecting motion of the subject's head.

Figure 5E:
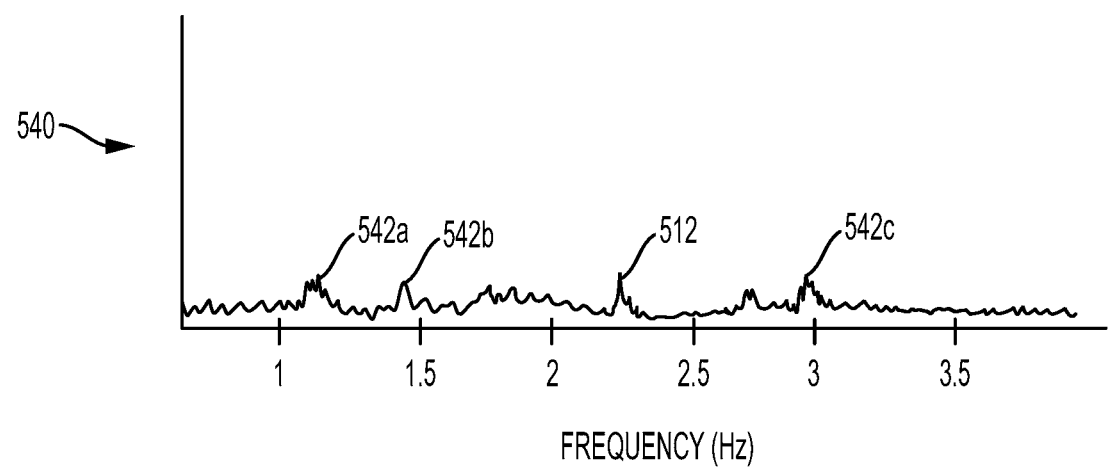
FIG. 5E is a frequency spectra plot of the second photoplethysmography signal after filtering, according to an example embodiment.

Similar to FIGS. 4A-4E above, FIGS. 5A-5E illustrate example signals obtained using light sensors and motion sensors, but in the context of an ear-mountable device rather than a wrist-mountable device. Specifically, FIG. 5A illustrates an example signal 500 output by a light sensor of the ear-mountable device, FIG. 5B illustrates an example frequency spectra plot 510 of the light sensor output 500, FIG. 5C illustrates an example signal 520 output by the motion sensor of the ear-mountable device, FIG. 5D illustrates an example frequency spectra plot 530 of the motion sensor output 520, and FIG. 5E illustrates an example frequency spectra plot 540 of the light sensor output 500 after filtering the light sensor output 500 to remove the spectral components identified from the motion sensor output 520.

The ear-mountable device may be configured to process these example signals in a manner similar to that described above in the context of the wrist-mountable device. For instance, referring to FIG. 5A, the light sensor output signal 500 of the ear-mountable device may include a number of peaks 502*a-c* that correspond with changes in reflected light caused by changes in blood volume in the subsurface vasculature and, thus, correspond with a heart rate of the subject; and the light sensor output signal 500 of the ear-mountable device may further include a number of motion artifact peaks 504*a-d* caused by motion of the subject's head. As shown in FIG. 5B, the frequency spectra plot 510 of the light sensor output 500 may include a heart rate frequency peak 512 corresponding to a frequency of the heart rate peaks 502*a-c*, and the frequency spectra plot 510 may include a motion frequency peak 514 corresponding to a frequency of the motion artifacts 504*a-d*.

In order to filter out the spectral components corresponding to the motion artifacts 504*a-d*, the ear-mountable device may take into consideration the output signal 520 of the motion sensor of the ear-mountable device. As shown in FIG. 5C, the motion sensor output signal 520 may include a number of peaks 522*a-d* corresponding to motion of the wearable device. For instance, if the subject is wearing the device in or on his or her ear while running, then the peaks 522*a-d* may correspond to each time the subject's head bobs up and down during a stride. Other examples are possible as well. Because the motion artifacts 504*a-d* in the light sensor output signal 500 correspond to motion of the wearable device, the motion artifacts 504*a-d* should have a similar occurrence frequency as the peaks 522*a-d* in the output signal 520 of the motion sensor. Referring to FIG. 5D, the frequency spectra plot 530 of the motion sensor output 520 includes a peak 532 corresponding to a dominant frequency of the motion sensor output 520, which corresponds to the frequency of the peaks 522*a-d* of the motion sensor output 520. By comparing the frequency spectra plot 530 of the motion sensor output 520 with the frequency spectra plot 510 of the light sensor output 500, it can be seen that frequency peak 532 of the motion sensor frequency spectra plot 530 aligns with frequency peak 514 of the light sensor frequency spectra plot 510.

Accordingly, the ear-mountable device may identify one or more spectral components of the motion sensor output 520 (e.g., by using an FFT algorithm to identify one or more dominant frequencies of the motion sensor output 520), and the device may then filter the light sensor output signal 500 and/or the frequency spectra signal 510 to remove the identified spectral components. This is shown in FIG. 5E where the frequency peak 514 corresponding to the frequency of the motion artifacts 504*a-d* is no longer present, while the frequency peak 512 corresponding to the frequency of the heart rate peaks 502*a-c* is preserved. However, other artifacts may still remain, such as those having spectral components 542*a-c*.

In order to distinguish the spectral components of the subject's heart rate from unwanted artifacts, the filtered frequency spectra plot 440 of the wrist-mountable device can be compared with the filtered frequency spectra plot 540 of the ear-mountable device. Because the wrist-mountable device and the ear-mountable device are mounted to different body parts, the devices may undergo different types of motion. Accordingly, the artifacts that appear in the output signals of their respective light sensors may have different spectral components. For instance, spectral components 442*a-b* of artifacts detected by the wrist-mountable device have a different frequency than spectral components 542*a-c* of artifacts detected by the ear-mountable device. However, because both the wrist-mountable device and the ear-mountable device are concurrently measuring the heart rate of the subject, each filtered frequency spectra plot should include a spectral component at the frequency of the subject's heart rate. For instance, both the filtered frequency spectra plot 440 of the wrist-mountable device and the filtered frequency spectra plot 540 of the ear-mountable device include a spectral component having a frequency of approximately 2.25 Hz (i.e., spectral components 412 and 512). Accordingly, either or both of the wearable devices may determine that the subject's heart rate is 2.25 Hz (or 135 bpm) based on the filtered frequency spectra plots each having a spectral component at that frequency.

Figure 6:
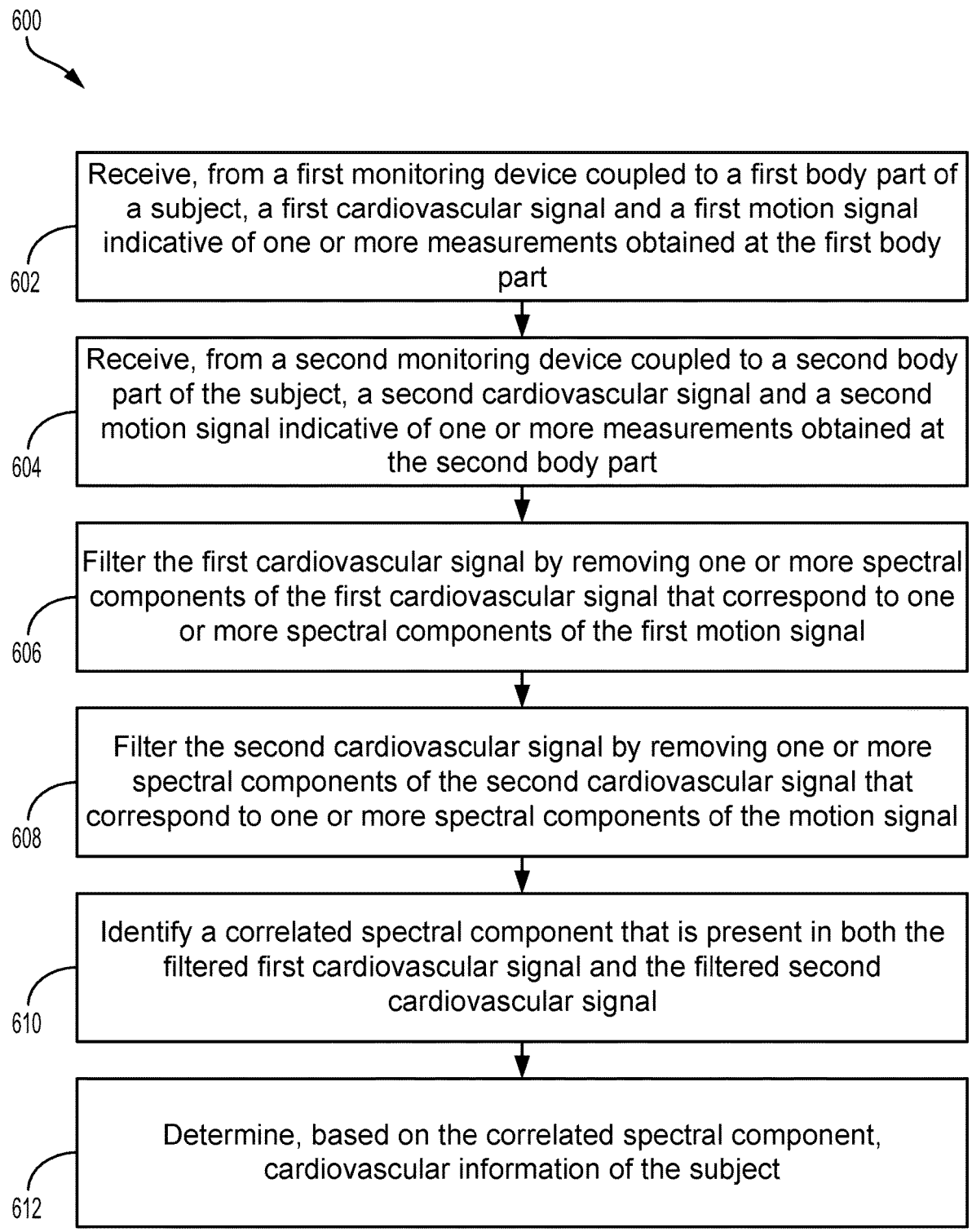
FIG. 6 is a flow chart of a method, according to an example embodiment.

FIG. 6 is a flow chart of an example method 600 that can be carried out in accordance with the present disclosure to determine one or more cardiovascular characteristics of a subject.

At block 602, the method 600 includes receiving, from a first monitoring device coupled to a first body part of a subject, a first cardiovascular signal and a first motion signal indicative of one or more measurements obtained at the first body part. In line with the discussion above, the first monitoring device may be a wrist-mountable device mounted to the subject's wrist, and the wrist-mountable device may generate the first cardiovascular signal and the first motion signal from measurements taken at the subject's wrist. The first cardiovascular signal may be a PPG signal generated by using a light source and a light sensor, and the first motion signal may be generated using an IMU or an accelerometer.

At block 604, the method 600 includes receiving, from a second monitoring device coupled to a second body part of the subject, a second cardiovascular signal and a second motion signal indicative of one or more measurements obtained at the second body part. In line with the discussion above, the second monitoring device may be an ear-mountable device mounted to the subject's ear, and the ear-mountable device may generate the second cardiovascular signal and the second motion signal from measurements taken at the subject's ear. The second cardiovascular signal may be a PPG signal generated by using a light source and a light sensor, and the second motion signal may be generated using an IMU or an accelerometer.

At block 606, the method 600 includes filtering the first cardiovascular signal by removing one or more spectral components of the first cardiovascular signal that correspond to one or more spectral components of the first motion signal. In line with the discussion above, this may involve transforming the first motion signal using an FFT algorithm to identify the one or more spectral components of the first motion signal. For instance, the identified spectral components could include any spectral component of the transformed first motion signal having a threshold high magnitude relative to other spectral components. By removing the identified spectral components from the first cardiovascular signal, certain artifacts that appear in the first cardiovascular signal due to motion of the subject's wrist or due to other sources unrelated to the subject's heart rate may be removed from the first cardiovascular signal.

At block 608, the method 600 includes filtering the second cardiovascular signal by removing one or more spectral components of the second cardiovascular signal that correspond to one or more spectral components of the second motion signal. In line with the discussion above, this may involve transforming the second motion signal using an FFT algorithm to identify the one or more spectral components of the second motion signal. For instance, the identified spectral components could include any spectral component of the transformed second motion signal having a threshold high magnitude relative to other spectral components. By removing the identified spectral components from the second cardiovascular signal, certain artifacts that appear in the second cardiovascular signal due to motion of the subject's head or due to other sources unrelated to the subject's heart rate may be removed from the second cardiovascular signal.

At block 610, the method 600 includes identifying a correlated spectral component that is present in both the filtered first cardiovascular signal and the filtered second cardiovascular signal. And at block 612, the method 600 includes determining, based on the correlated spectral component, cardiovascular information of the subject. In line with the discussion above, while the filtered first cardiovascular signal and the filtered second cardiovascular signal may include various other spectral components associated with artifacts in the first and second cardiovascular signals that were not filtered out at blocks 606 and 608, the filtered first cardiovascular signal and the filtered second cardiovascular signal both include a correlated spectral component that corresponds to a heart rate of the subject. Accordingly, by identifying the correlated spectral component that is present in both the first and second filtered cardiovascular signals, the subject's heart rate may be determined.

The method 600 could include additional or alternative steps. In some examples, the method 600 could include providing, to a user, an indication of the determined cardiovascular information. For instance, the method 600 could include displaying a graphical or textual representation of the cardiovascular information. As another example, the method 600 could include generating and outputting an audio or visual alert based on the cardiovascular information, such as in response to determining that the subject's heart rate is above a threshold high value and/or below a threshold low value. The method 600 could include transmitting indications of the determined cardiovascular information to a remote system (e.g., a server or a cloud computing service) and receiving, from the remote system, a health state or other information about the user determined, based on the cardiovascular information, by the remote system.

In another example method, instead of separately filtering motion spectral components out of the cardiovascular signals generated by the wrist-mountable device and the ear-mountable device, the cardiovascular signals from the devices may be combined, and the combined signal may be filtered to remove spectral components identified based on motion sensors located on each device.

Figure 7:
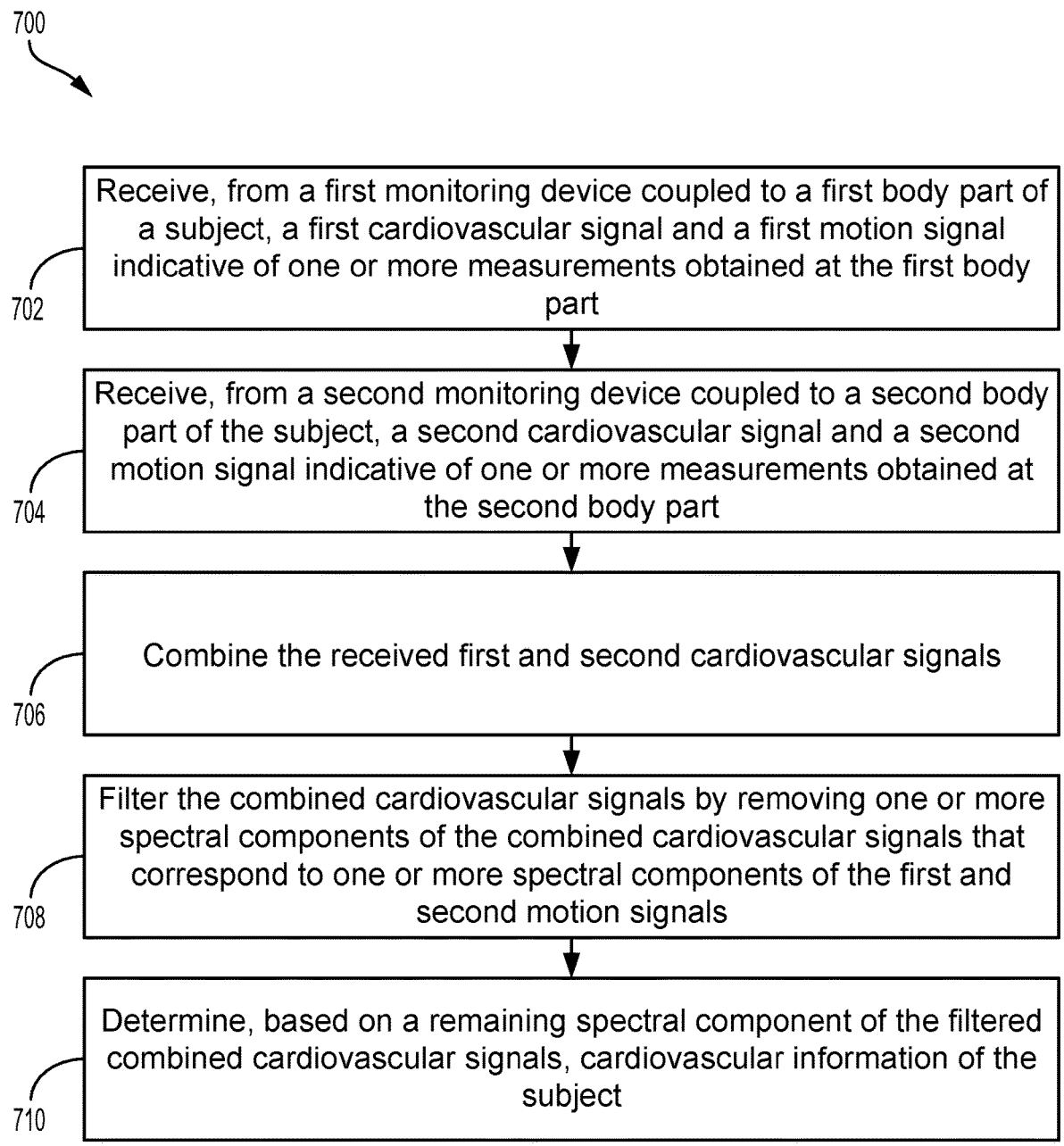
FIG. 7 is a flow chart of another method, according to an example embodiment.

FIG. 7 is a flow chart of such an example method 700 that can be carried out in accordance with the present disclosure to determine one or more cardiovascular characteristics of a subject.

At block 702, the method 700 includes receiving, from a first monitoring device coupled to a first body part of a subject, a first cardiovascular signal and a first motion signal indicative of one or more measurements obtained at the first body part. In line with the discussion above, the first monitoring device may be a wrist-mountable device mounted to the subject's wrist, and the wrist-mountable device may generate the first cardiovascular signal and the first motion signal from measurements taken at the subject's wrist. The first cardiovascular signal may be a PPG signal generated by using a light source and a light sensor, and the first motion signal may be generated using an IMU or an accelerometer.

At block 704, the method 700 includes receiving, from a second monitoring device coupled to a second body part of the subject, a second cardiovascular signal and a second motion signal indicative of one or more measurements obtained at the second body part. In line with the discussion above, the second monitoring device may be an ear-mountable device mounted to the subject's ear, and the ear-mountable device may generate the second cardiovascular signal and the second motion signal from measurements taken at the subject's ear. The second cardiovascular signal may be a PPG signal generated by using a light source and a light sensor, and the second motion signal may be generated using an IMU or an accelerometer.

At block 706, the method 700 includes combining the received first and second cardiovascular signals, such as by feeding the first and second cardiovascular signals into a summing amplifier or the like.

At block 708, the method 700 includes filtering the combined cardiovascular signals by removing one or more spectral components of the combined cardiovascular signals that correspond to one or more spectral components of the first and second motion signals. In line with the discussion above, this may involve transforming the first motion signal and the second motion signal using an FFT algorithm to identify the one or more spectral components of the first and second motion signals. For instance, the identified spectral components could include any spectral component of the transformed first and second motion signals having a threshold high magnitude relative to other spectral components. By removing the identified spectral components from the combined cardiovascular signals, certain artifacts that appear in the combined cardiovascular signals due to motion of the subject's wrist, motion of the subject's head, or due to other sources unrelated to the subject's heart rate may be removed from the combined cardiovascular signals.

At block 710, the method 700 includes determining, based on a remaining spectral component of the filtered combined cardiovascular signals, cardiovascular information of the subject. This may involve identifying the strongest remaining spectral component of the filtered combined cardiovascular signals. Because the spectral components from both the first and second motion signals have been removed from the combined cardiovascular signals, the strongest remaining spectral component likely corresponds to the subject's heart pumping. Accordingly, the determined cardiovascular information may include the subject's heart rate, and the determined heart rate may be equivalent to the frequency of the remaining spectral component of the filtered combined cardiovascular signals.

The method 700 could include additional or alternative steps. In some examples, the method 700 could include providing, to a user, an indication of the determined cardiovascular information. For instance, the method 700 could include displaying a graphical or textual representation of the cardiovascular information. As another example, the method 700 could include generating and outputting an audio or visual alert based on the cardiovascular information, such as in response to determining that the subject's heart rate is above a threshold high value and/or below a threshold low value. The method 700 could include transmitting indications of the determined cardiovascular information to a remote system (e.g., a server or a cloud computing service) and receiving, from the remote system, a health state or other information about the user determined, based on the cardiovascular information, by the remote system.

It should be understood that, where possible, the operations described herein may be performed by any one and/or multiple ones of the systems and/or devices described herein. For instance, in some examples, the wrist-mountable device may include a controller for obtaining the first cardiovascular signal and the first motion signal and for filtering the first cardiovascular signal to remove one or more spectral components of the first motion signal. Similarly, the ear-mountable device may include a controller for obtaining the second cardiovascular signal and the second motion signal and for filtering the second cardiovascular signal to remove one or more spectral components of the second motion signal. The wrist-mountable device and the ear-mountable device may subsequently engage in wired or wireless communication for exchanging information associated with the filtered signals and identifying the correlated spectral component. For instance, the ear-mountable device may transmit information indicative of the filtered first cardiovascular signal to the wrist-mountable device, and the wrist-mountable device may use the transmitted information to identify the correlated spectral component. In other examples, data may be transmitted to a single device, and the operations described herein may be performed by that single device. For instance, the ear-mountable device may transmit the first cardiovascular signal and/or the first motion signal (or information indicative thereof) to the wrist-mountable device. The controller of the wrist-mountable device may subsequently perform some or all of the operations described herein. Other examples are possible as well.

Further, while the specific embodiments disclosed herein are related to a wrist-mountable device and an ear-mountable device, various other wearable devices may alternatively or additionally be used in accordance with the methods described herein. For example, the wrist-mountable device and/or the ear-mountable device could be replaced by any device that is capable of being worn at, on or in proximity to a body surface, such as an ankle, waist, chest, or other body part.

Still further, while the specific embodiments disclosed herein related to the use of two wearable devices, the disclosed concepts could be extended to any number of wearable devices. For instance, a third wearable device could provide a third cardiovascular signal and a third motion signal; the third cardiovascular signal could be filtered to remove one or more spectral components of the third motion signal; and cardiovascular information of the subject could be determined based on a correlated spectral component that is present in the filtered first, second, and third cardiovascular signals.

IV. Conclusion

Where example embodiments involve information related to a person or a device of a person, the embodiments should be understood to include privacy controls. Such privacy controls include, at least, anonymization of device identifiers, transparency and user controls, including functionality that would enable users to modify or delete information relating to the user's use of a product.

Further, in situations in where embodiments discussed herein collect personal information about users, or may make use of personal information, the users may be provided with an opportunity to control whether programs or features collect user information (e.g., information about a user's medical history, social network, social actions or activities, profession, a user's preferences, or a user's current location), or to control whether and/or how to receive content from the content server that may be more relevant to the user. In addition, certain data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location of a user cannot be determined. Thus, the user may have control over how information is collected about the user and used by a content server.

The particular arrangements shown in the figures should not be viewed as limiting. It should be understood that other embodiments may include more or less of each element shown in a given figure. Further, some of the illustrated elements may be combined or omitted. Yet further, an exemplary embodiment may include elements that are not illustrated in the figures.

Additionally, while various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims. Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are contemplated herein.

What is claimed is:
1. A system comprising:
a first monitoring device configured to couple to a first body part of a subject, wherein the first monitoring device comprises a first photoplethysmographic (PPG) sensor configured to measure a first cardiovascular signal at the first body part and a first accelerometer configured to measure a first motion signal at the first body part, wherein the first body part of the subject is an ear of the subject, and wherein the first monitoring device comprises an earphone configured to be worn on or in the ear of the subject;

a second monitoring device configured to couple to a second body part of the subject, wherein the second monitoring device comprises a second PPG sensor configured to measure a second cardiovascular signal at the second body part and a second accelerometer configured to measure a second motion signal at the second body part, wherein the second body part of the subject is a wrist of the subject, and wherein the second monitoring device comprises a wristband configured to be worn around the wrist of the subject; and a controller configured to:
receive the first and second cardiovascular signals and the first and second motion signals from the first and second monitoring devices;
filter the first cardiovascular signal by removing one or more spectral components of the first cardiovascular signal that correspond to one or more spectral components of the first motion signal;
filter the second cardiovascular signal by removing one or more spectral components of the second cardiovascular signal that correspond to one or more spectral components of the second motion signal;
compare the filtered first cardiovascular signal and the filtered second cardiovascular signal to identify a spectral component that is present in both the filtered first cardiovascular signal and the filtered second cardiovascular signal during operation of the system;
determine, based on the identified spectral component, cardiovascular information of the subject; and
communicate with a user interface to cause the user interface to provide notification of a health state associated with the subject based on the determined cardiovascular information of the subject.

2. The system of claim 1, wherein the first cardiovascular signal comprises: (i) a first pulse rate component attributable to a blood pulse rate in the first body part and (ii) a first artifact component not attributable to the blood pulse rate in the first body part, and wherein removing one or more spectral components of the first cardiovascular signal that correspond to one or more spectral components of the first motion signal comprises removing the first artifact component from the first cardiovascular signal; and wherein the second cardiovascular signal comprises: (i) a second pulse rate component attributable to a blood pulse rate in the second body part and (ii) a second artifact component not attributable to the blood pulse rate in the second body part, and wherein removing one or more spectral components of the second cardiovascular signal that correspond to one or more spectral components of the second motion signal comprises removing the second artifact component from the second cardiovascular signal.

3. The system of claim 1, wherein the controller configured to determine the cardiovascular information of the subject comprises the controller being configured to determine a heart rate of the subject based on a frequency of the identified spectral component.

4. The system of claim 1, wherein the first monitoring device comprises the earphone having the first PPG sensor configured to measure a blood pulse rate in the ear of the subject.

5. The system of claim 1, wherein the wristband comprises the second PPG sensor configured to measure a blood pulse rate in the wrist of the subject.

6. The system of claim 1, wherein the controller configured to filter the first cardiovascular signal comprises the controller being configured to compare a first frequency spectrum of the first accelerometer with a first frequency spectrum of the first PPG sensor.

7. The system of claim 6, wherein the controller configured to filter the second cardiovascular signal comprises the controller being configured to compare a second frequency spectrum of the second accelerometer with a second frequency spectrum of the second PPG sensor.

8. The system of claim 1, wherein when comparing the filtered first cardiovascular signal and the filtered second cardiovascular signal the controller is further configured to compare a first frequency spectrum of the filtered first cardiovascular signal with a second frequency spectrum of the filtered second cardiovascular signal to identify a spectral peak at a frequency that is common to the first and second frequency spectrums.

9. A method comprising:
receiving, from a first monitoring device coupled to a first body part of a subject, a first cardiovascular signal and a first motion signal, wherein the first cardiovascular signal is indicative of one or more measurements obtained at the first body part using a first photoplethysmographic (PPG) sensor of the first monitoring device, and wherein the first motion signal is indicative of one or more measurements obtained at the first body part using a first accelerometer of the first monitoring device, wherein the first body part of the subject is an ear of the subject, and wherein the first monitoring device comprises an earphone worn on or in the ear of the subject;
receiving, from a second monitoring device coupled to a second body part of the subject, a second cardiovascular signal and a second motion signal, wherein the second cardiovascular signal is indicative of one or more measurements obtained at the second body part using a second PPG sensor of the second monitoring device, and wherein the second motion signal is indicative of one or more measurements obtained at the second body part using a second accelerometer of the second monitoring device, wherein the second body part of the subject is a wrist of the subject, and wherein the second monitoring device comprises a wristband configured to be worn around the wrist of the subject;
filtering the first cardiovascular signal by removing one or more spectral components of the first cardiovascular signal that correspond to one or more spectral components of the first motion signal;
filtering the second cardiovascular signal by removing one or more spectral components of the second cardiovascular signal that correspond to one or more spectral components of the second motion signal;
comparing the filtered first cardiovascular signal and the filtered second cardiovascular signal to identify a spectral component that is present in both the filtered first cardiovascular signal and the filtered second cardiovascular signal during operation of the first monitoring device or the second monitoring device;
determining, based on the identified spectral component, cardiovascular information of the subject; and
causing a user interface to provide notification of a health state associated with the subject based on the determined cardiovascular information of the subject.

10. The method of claim 9, further comprising:
measuring, using the first monitoring device, the first cardiovascular signal and the first motion signal at the first body part; and
measuring, using the second monitoring device, the second cardiovascular signal and the second motion signal at the second body part.

11. The method of claim 9, wherein the first cardiovascular signal comprises: (i) a first pulse rate component attributable to a blood pulse rate in the first body part and (ii) a first artifact component not attributable to the blood pulse rate in the first body part, and wherein removing one or more spectral components of the first cardiovascular signal that correspond to one or more spectral components of the first motion signal comprises removing the first artifact component from the first cardiovascular signal; and
wherein the second cardiovascular signal comprises: (i) a second pulse rate component attributable to a blood pulse rate in the second body part and (ii) a second artifact component not attributable to the blood pulse rate in the second body part, and wherein removing one or more spectral components of the second cardiovascular signal that correspond to one or more spectral components of the second motion signal comprises removing the second artifact component from the second cardiovascular signal.

12. The method of claim 9, wherein determining the cardiovascular information of the subject comprises determining a heart rate of the subject based on a frequency of the identified spectral component.

* * * * *